United States Patent [19]

Sauer et al.

[11] Patent Number: 4,503,261

[45] Date of Patent: Mar. 5, 1985

[54] PREPARATION OF GLYOXAL

[75] Inventors: Wolfgang Sauer, Kirchheimbolanden; Klaus Halbritter, Mannheim; Heinz Engelbach, Limburgerhof, all of Fed. Rep. of Germany

[73] Assignee: BASF Aktiengesellschaft, Fed. Rep. of Germany

[21] Appl. No.: 400,690

[22] Filed: Jul. 22, 1982

[51] Int. Cl.³ ............................................. C07C 45/38
[52] U.S. Cl. .................................................... 568/471
[58] Field of Search ......................................... 568/471

[56] References Cited

U.S. PATENT DOCUMENTS

| 2,051,266 | 8/1936 | McAllister et al. | 568/471 |
| 3,948,997 | 4/1976 | Howe et al. | 568/471 |
| 4,242,282 | 12/1980 | Diem et al. | 568/471 |
| 4,258,216 | 3/1981 | Trecek et al. | 568/471 |
| 4,302,609 | 3/1981 | Baltes et al. | 568/471 |

FOREIGN PATENT DOCUMENTS

| 7570 | 2/1980 | European Pat. Off. | 568/471 |
| 1923048 | 6/1969 | Fed. Rep. of Germany | 568/471 |
| 1967147 | 6/1969 | Fed. Rep. of Germany | 568/471 |
| 2153343 | 5/1972 | Fed. Rep. of Germany | 252/4 |
| 2634439 | 1/1978 | Fed. Rep. of Germany | 568/471 |
| 2922599 | 12/1980 | Fed. Rep. of Germany | 568/471 |
| 836828 | 6/1960 | United Kingdom | 568/471 |
| 12752592 | 5/1972 | United Kingdom | 568/471 |

Primary Examiner—Werren B. Lone
Attorney, Agent, or Firm—Keil & Weinkauf

[57] ABSTRACT

A process for the continuous preparation of glyoxal by oxidation of ethylene glycol, in which the ethylene glycol, oxygen and an inert gas are passed, at from 450° to 800° C., over a catalyst consisting of one or more layers of copper crystals and one or more layers of silver crystals, the copper and silver crystals having a particle size of from 0.1 to 2.5 mm.

6 Claims, 1 Drawing Figure

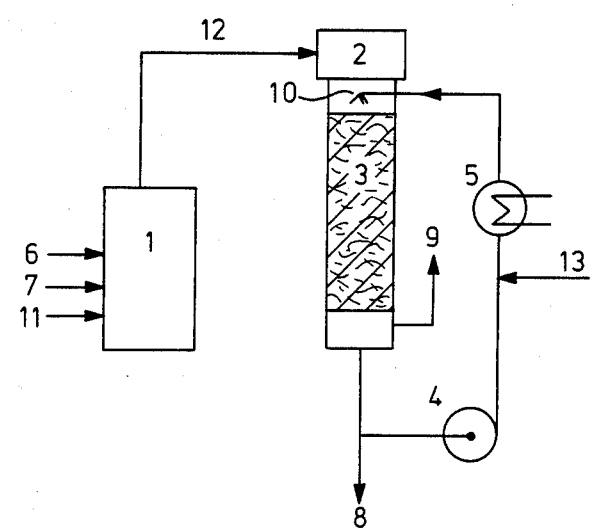

PREPARATION OF GLYOXAL

The present invention relates to a novel process for the preparation of glyoxal by oxidation of glycol in the presence of a copper/silver layered catalyst.

German Pat. No. 1,923,048 discloses that glyoxal can be prepared by vapor phase oxidation of ethylene glycol over an oxidation catalyst containing copper in combination with tin, phosphorus, arsenic, antimony or bismuth. The catalyst may also contain silver and is used in the form of an alloy, preferably as turnings or gauze. Yields of from 55% to 72%, relative to the ethylene glycol reacted, are given for the combination silver/copper/phosphorus. However, the higher yields can only be achieved at the price of an incomplete conversion of the glycol. This is unsatisfactory from an economic point of view, since the residual glycol can be removed from the product only at great expense. Moreover, inadequate space/time yields are obtained in this conventional process, and the involved preparation of the catalyst is also a disadvantage.

German Pat. No. 1,967,147 discloses a silver catalyst, containing phosphorus, for the preparation of glyoxal from ethylene glycol. In this process also, a satisfactory degree of conversion must be sacrificed for a glyoxal yield of up to 70%, based on the ethylene glycol reacted. The space/time yields are also unsatisfactory.

There has been no lack of attempts to overcome the disadvantages described. Thus, German Laid-Open Application DOS No. 2,634,439 proposes the addition of a bromine compound to the reaction mixture when phosphorus-containing copper and/or silver catalysts are used. Although the glyoxal yield can thus be increased to 80.5%, with almost complete conversion, the space/time yields still leave something to be desired in this process. Moreover, the corrosive bromine compounds added at reaction temperatures of about 450° C. and in the presence of oxygen cause serious corrosion problems, and the fact that the copper-containing catalysts age rapidly, causing a drop in yield, is also a disadvantage.

German Laid-Open Application DOS No. 2,158,343 reports that the selectivity of catalysts disclosed in German Pat. No. 1,923,048 falls, from an initial value of from 60 to 64%, to 55% over an operating period of 700 hours. It also states that, after such an operating period, a catalyst containing copper, silver and phosphorus can be regenerated by reduction at 450° C. for 12 hours. Germain Laid-Open Application DOS No. 2,158,344 discloses the regeneration of a catalyst containing copper and phosphorus, in which an excess of oxygen is passed over the catalyst for not less than 1 day. These regeneration processes have the disadvantage that they involve a shutdown of production and necessitate expensive safety measures in order to prevent the air used for the regeneration from becoming mixed with the reaction gas.

In the process disclosed in German Laid-Open Application DOS No. 2,832,405, the life of copper catalysts is substantially increased if the vapor phase oxidation of ethylene glycol is carried out at from 225° to 500° C. in the presence of a phosphorus compound which is volatile under the reaction conditions, eg. trimethyl phosphate, the amount of phosphorus (calculated as P), based on the amount by weight of ethylene glycol, being from 1 to 100 ppm. The catalysts are employed in this process in the form of turnings, wire mesh or gauze, or as supported catalysts. Although this process leads to a substantial reduction in the loss of catalyst activity, it does not achieve long-lasting stabilization of the activity at a high level.

German Laid-Open Application DOS No. 2,803,318 discloses a process for the preparation of glyoxal from glycol, wherein the oxidation is carried out over silver crystals having a particle size of from 0.1 to 2.5 mm, with a residence time of not more than 0.5 second and at from 447° to 707° C. Although the space/time yields achieved in this process are many times higher than those obtained in the processes described above, the relatively low yield of only 55% is a disadvantage. The yield can be improved by adding bromoform to the starting mixture, but at the price of corrosion problems and difficulties in respect of product purity.

In contrast, the yield can be improved if the hot reaction gases are condensed with water or an aqueous glyoxal solution by the process disclosed in German Laid-Open Application DOS No. 2,922,599. This treatment of the reaction gases increases the yield of glyoxal, based on the glycol employed, from 55% to as much as 62%, at a conversion of about 98% and without the addition of bromine compounds. Moreover, glyoxal can be prepared directly in the commercial form of a 40% strength aqueous solution by this process, and, in comparison with the process of German Laid-Open Application DOS No. 2,803,318, the color number of the glyoxal is substantially improved and the safety of operation is greatly increased by avoiding blockages in the condensation section. The disadvantage of this process is, however, the contamination of the resulting aqueous glyoxal solution with glycolaldehyde, for the removal of which no economically acceptable methods are available.

The conventional processes for the preparation of glyoxal by catalytic oxidation of ethylene glycol are thus unsatisfactory from the point of view of the desired uncomplicated and economic operation, simple preparation of the catalyst, long catalyst life, good yield and space/time yield and purity of the product.

We have found that in the continuous preparation of glyoxal by oxidation of ethylene glycol in which the ethylene glycol, oxygen and an inert gas are passed at from 450° to 800° C. over a catalyst consisting of copper and silver, particularly advantageous results are obtained if the catalyst consists of one or more layers of copper crystals and one or more layers of silver crystals, the copper and silver crystals having a particle size of from 0.1 to 2.5 mm.

In the novel process, the glycol is oxidized with oxygen in the presence of an inert gas, eg. nitrogen, in a molar ratio of inert gas to oxygen of, for example, not less than 4.4:1. The molar ratio of oxygen to ethylene glycol is advantageously from 0.7:1 to 1.4:1. The indicated reaction temperatures of from 450° to 800° C. are the temperatures arising in the catalyst bed. The residence time of the reaction mixture in the catalyst bed should not exceed 0.05 second.

In the process according to the invention, the oxidation is carried out over a multi-layer catalyst containing one or more layers of copper crystals and one or more layers of silver crystals. The total thickness of the catalyst bed is from 5 to 100 mm, preferably from 20 to 40 mm. The catalyst layers are arranged in the reactor, which usually stands vertical. The vaporous starting mixture of ethylene glycol and oxygen or air is generally passed from the top downwards, so that the top layer is also the section of catalyst exposed to the starting mixture. All the statements describing the upper and lower sections of the catalyst apply by analogy to reactors of different construction, for example reactors arranged horizontally, or to a different flow path of the starting material.

The catalyst contains from 10 to 45% by weight, in particular from 20 to 30% by weight and particularly preferably 25% by weight, of copper crystals and from 55 to 90% by weight, in particular from 70 to 80% by weight and particularly preferably 75% by weight, of silver crystals, based on the total weight of all the catalyst particles.

The number of layers of copper crystals can be larger than, the same as or smaller than the number of layers of silver crystals. For example, the multi-layer catalyst consists of from one to four, preferably two or three, layers of copper crystals and from one to four, preferably two or three, layers of silver crystals. The crystals have a particle size of from 0.1 to 2.5 mm, particle size fractions of, for example, from 0.2 to 0.4 mm, from 0.4 to 0.75 mm, from 0.75 to 1.0 mm and from 1.0 to 2.5 mm being used for the individual layers.

The particle sizes of two adjacent layers can increase, remain the same, for example when passing from a copper layer to a silver layer or vice versa, or decrease, in the direction of flow.

One or more layers of copper crystals can be arranged above and/or below each layer of silver crystals. Preferably, only two or three layers of copper are used, and they are arranged above and/or below the upper layer of silver.

Each individual layer of silver or copper is usually arranged uniformly, so that the thickness of the individual layer is the same over the entire cross-section. The thickness then depends directly on the proportions by weight in the whole catalyst and on the particular particle size. However, all or several layers or, advantageously, one layer of copper or silver can also be arranged non-uniformly. This is effected, for example, by placing most of the catalyst particles in the center, at the side or, advantageously, at the edge of the layer and distributing only a relatively small residual amount about the remainder of the layer. The thicknesses of two adjacent layers can be the same or can increase or decrease in the direction of flow.

We have also found that the formation of carbon dioxide which proceeds as an undesirable side reaction can be decreased and the yield of glyoxal can be increased if the oxidation over the copper/silver layered catalyst is carried out in the presence of a phosphorus compound which is volatile under the reaction conditions. Since the addition of the phosphorus compound must be calculated so that it suppresses the formation of carbon dioxide but does not lead to deactivation of the catalyst in respect of the formation of glyoxal from glycol, the amount added in the process according to the invention is such that the amount of phosphorus (calculated as P) is from 0.5 to 20 ppm, based on the amount by weight of ethylene glycol.

Examples of suitable phosphorus compounds which are volatile under the reaction conditions are trimethyl phosphate, triethyl phosphate, tri-isopropyl phosphate, tri-n-propyl phosphate, trimethyl phosphite, triethyl phosphite, triethylphosphine oxide, diethyl methylphosphonate, dimethyl methylphosphonate and diethyl ethylphosphonate.

The vaporous reaction mixture obtained in the catalytic oxidation is worked up in a conventional manner, for example by bringing it into contact, immediately after it has left the catalyst bed, with a liquid which causes instant condensation of the oxidation products. Suitable condensation liquids are water, the condensed liquid reaction mixture or a mixture of these two liquids. It is particularly advantageous to use the condensed reaction mixture as the condensation liquid, in which case the excess condensate which is not recycled as the cooled condensation liquid is removed as the crude product and, where relevant, passed for working up or further reaction.

The vaporous reaction mixture is at from 320° to 650° C. and is advantageously brought into contact with the condensation liquid within one second. The temperature of the condensation liquid is, for example, from −20° to 80° C. This treatment is carried out by, for example, passing the stream of hot reaction gases directly into a quenching chamber immediately downstream of the catalyst bed. Preferably, droplets of the condensation liquid having an average diameter of from 1 to 2,000 micrometers are brought into contact with the reaction gases. The droplets are produced with the aid of a conventional atomizing apparatus, in particular a nozzle. The condensation liquid is advantageously sprayed into the quenching chamber so that most of the droplets meet the stream of reaction gases at an angle of from 2° to 85° C. to the axis of flow.

Advantageously, from 20 to 100 parts by weight of condensation liquid (called quenching liquid in the Examples) are used per part by weight of reaction gases.

The process according to the invention gives a better overall result in respect of yield, space/time yield, product purity and catalyst life in a simpler and more economical manner than the conventional processes. The preparation and working up of the catalyst are particularly simple. Thus, copper and silver crystals of the required particle size such as are prepared by electrolysis can be used directly.

In the process according to the invention, the long-life copper/silver layered catalyst can easily be replaced if such replacement should after all be necessary. Thus, the layers of copper and silver can be separated mechanically, for example simply by inserting copper, silver or stainless steel mesh between the layers of copper and silver. Both the copper and the silver can then be converted back into the catalytically active form, almost without loss, by electrolysis.

The glyoxal obtained in the process according to the invention, where relevant directly in the commercial form of a 40% strength aqueous solution, is a product with a comparatively high quality which remains unchanged even over a long period of operation. Thus, the 40% strength glyoxal solution has a residual content of unreacted glycol of less than 0.1% and a glycolaldehyde content and formaldehyde content of only about 1% each. Since the color number and acid number of the glyoxal solutions also fulfill the high requirements of the textile, paper and leather industries, no particular purification stage, for example using ion exchangers, is necessary in the process according to the invention. The process also avoids the addition of halogen compounds as inhibitors and the associated danger of corrosion.

The exceptionally good space/time yield of the process according to the invention, which enables the reactor volume to be kept extremely low in comparison with the conventional glyoxal processes and reduces capital investment, is particularly noteworthy. Together with the high yield of glyoxal, this makes the process according to the invention highly profitable.

These advantageous results are surprising. Thus, it was not to be expected that simply combining pure copper and silver crystals of a particular particle size in the form of layers would permit such a substantial increase in the rate of reaction, and thus in the space/time yield, in comparison with the conventional use of silver/copper alloys with other additives (promoters). It is also surprisingly that, in comparison with the use of pure silver crystals, not only is the yield substantially increased but also the level of by-products is at the same time drastically reduced. The yield-increasing effect of volatile phosphorus compounds is also surprising, since German Laid-Open Application DOS No. 2,832,405 mentions an advantageous effect of volatile phosphorus compounds only in the context of prolonging the life of copper catalysts.

No noticeable loss in activity of the copper/silver layered catalysts used in the process according to the invention occurs during prolonged operation, so that measures to extend the life of the catalysts are superfluous. It is therefore surprising that the addition of volatile phosphorus compounds increases the yield by a certain amount by reducing the formation of carbon dioxide.

In the Examples which follow, parts are by weight.

EXAMPLE 1

(The numerals in parentheses relate to the drawing)

An apparatus with an ethylene glycol vaporizer (1), appropriate leads for ethylene glycol (6), water (7) and air or oxygen (11) and a vertical tube reactor (2) is used. The head of the reactor includes the lead (12) for the vaporous starting mixture and the reactor hood. The catalyst bed is below the head of the reactor, and below the bed is the quenching chamber (10), which forms the head of a packed column (3). Some of the condensate is used as the quenching liquid, which is sprayed by means of a pump (4) via a heat exchanger (5) and a nozzle system immediately downstream of the catalyst bed into the hot gases, which are cooled in the quenching chamber and partially condensed, so that the glyoxal solution can be removed via line (8). The waste gas escapes via line (9).

A catalyst of copper and silver crystals (41 parts) having the composition which follows is introduced into the reactor (2) (sequence of the layers from the top downwards in the direction of flow of the gases):

|  | Material | Particle size (mm) | Amount of catalyst (% by weight) |
| --- | --- | --- | --- |
| Layer 1 | Copper | 0.2–0.4 | 6.8 |
| Layer 2 | Copper | 0.4–0.75 | 18.6 |
| Layer 3 | Silver | 0.4–0.75 | 54.7 |
| Layer 4 | Silver | 1.0–2.5 | 19.9 |

The total height of the catalyst bed is 30 mm. A mixture of 220 parts of ethylene glycol, 220 parts of water, 536 parts of air and 1,576 parts of nitrogen per hour is passed to the vaporizer (1), where it is heated and vaporized. The vaporous starting mixture is passed through the catalyst and reacted at 600° C. under 1.2 bar. The residence time in the catalyst chamber is 0.006 second.

The flow rate of the reaction gases leaving the catalyst bed is 4.8 m per second. The quenching liquid is at 61° C. Water is initially used as the quenching liquid. Part of the quenching liquid, depending on the amount of condensed reaction mixture obtained, is removed continuously via line 8. The quenching liquid becomes more concentrated with condensed reaction mixture, and after a start-up phase reaches a steady concentration corresponding to the composition of the mixture. Balancing of the product solution removed continuously from the quenching circulation according to the amount of condensing reaction mixture is then started. 2 rings each with 6 nozzle arranged at intervals are used for atomizing the quenching liquid. The nozzles of one ring are on the wall of the column and are arranged symmetrically. The angle at which the droplets meet the axis of flow is different for each nozzle, and is from 15° to 75°. This angle is from 30° to 75° for 70% of the droplets. The average diameter of the droplets is 200 micrometers. 363 parts per hour of a 40 percent strength by weight glyoxal solution, ie. 145 parts of glyoxal per hour, are obtained, corresponding to a yield of 70.6% of theory, based on the glycol used. The life of the catalyst is 90 days. The glyoxal solution contains 0.05 percent by weight of ethylene glycol, 1.2 percent by weight of formaldehyde and 0.9 percent by weight of glycolaldehyde and has an acid number of 4 (amount of potassium hydroxide, in mg, required for neutralization of 1 g of glyoxal solution).

The conversion is 99.9 percent, the space/time yield is 15.4 g of glyoxal per $cm^3$ of catalyst volume per hour, and the color number of the solution after three days of operation is 12 (the color number is determined by means of the platinum/cobalt scale according to ASTM D 1209-69).

EXAMPLE 2

(Comparative Example in which the layered catalyst consists only of silver)

The same apparatus as in Example 1 is used. A layered catalyst is introduced into the reactor as in Example 1, but instead of the copper in layers 1 and 2, similar amounts of silver crystals of the same particle size are used.

The reaction and working up are carried out as described in Example 1. 386 parts per hour of a 32 percent strength by weight glyoxal solution, ie. 124 parts of glyoxal per hour, are obtained, corresponding to a yield of 60.3% of theory, based on the glycol used. The glyoxal solution contains 1.2 percent by weight of ethylene glycol, 0.9 percent by weight of formaldehyde and 6.1 percent by weight of glycolaldehyde and has an acid number of 4. The conversion is 97.9 percent, the space/time yield is 13.2 g of glyoxal per $cm^3$ of catalyst volume per hour, and the color number of the solution after three days of operation is 15.

EXAMPLE 3

(Comparative Example in which the layered catalyst consists only of copper)

The same apparatus as in Example 1 is used. A layered catalyst is introduced into the reactor as in Example 1, but instead of the silver in layers 3 and 4, similar amounts of copper crystals of the same particle size are used.

The reaction and working up are carried out as described in Example 1. 332 parts per hour of a 34 percent strength by weight glyoxal solution, ie. 113 parts of glyoxal per hour, are obtained, corresponding to a yield of 54.9% of theory, based on the glycol used. The glyoxal solution contains 3.7 percent by weight of ethylene glycol, 0.9 percent by weight of formaldehyde and 1.2 percent by weight of glycolaldehyde and has an acid number of 5. The conversion is 94.4 percent, the space/time yield is 12.0 g of glyoxal per cm³ of catalyst volume per hour, and the color number of the solution after three days of operation is 20.

EXAMPLE 4

(Comparative Example in which a mixture of copper and silver is used as the catalyst)

The same apparatus as in Example 1 is used. A mechanical mixture of copper and silver crystals with the same particle size distribution and weight distribution as given in Example 1 is introduced into the reactor as the catalyst. The total amount (41 parts) is the same as in Example 1. The bulk height of the catalyst is somewhat lower at 27 mm because of the higher bulk density of the mixture.

The reaction and working up are carried out as described in Example 1. 362 parts per hour of a 33 percent strength by weight glyoxal solution, ie. 119 parts of glyoxal per hour, are obtained, corresponding to a yield of 57.8% of theory, based on the glycol used. The glyoxal solution contains 1.9 percent by weight of ethylene glycol, 1.1 percent by weight of formaldehyde and 4.2 percent by weight of glycolaldehyde and has an acid number of 4.

The conversion is 96.9 percent, the space/time yield is 14.1 g of glyoxal per cm³ of catalyst volume per hour, and the color number of the solution after three days of operation is 15.

EXAMPLE 5

(Addition of a volatile phosphorus compound)

The same apparatus and the same multi-layer catalyst as in Example 1 are used. The reaction is carried out at 600° C. under 1.2 bar by a method similar to that described in Example 1, and in addition 0.003 part per hour of trimethyl phosphate, $(CH_3O)_3PO$ (corresponding to 3 ppm of P, based on the weight of ethylene glycol fed in), are added to the gas mixture flowing over the catalyst.

353 parts per hour of a 45 percent strength by weight glyoxal solution, ie. 159 parts of glyoxal per hour, are obtained, corresponding to a yield of 77.3% of theory, based on the glycol used. The life of the catalyst is 90 days. The glyoxal solution contains 0.05 percent by weight of ethylene glycol, 1.0% by weight of formaldehyde and 1.05% by weight of glycolaldehyde and has an acid number of 5.

The conversion is 99.9 percent, the space/time yield is 16.9 g of glyoxal per cm³ of catalyst volume per hour, and the color number of the solution after three days of operation is 11.

EXAMPLE 6

(Comparative Example with a larger amount of a volatile phosphorus compound)

The same apparatus as in Example 1 is used. A multi-layer catalyst of copper and silver similar to that in Example 1 is introduced into the reactor. The reaction is carried out at 600° C. under 1.2 bar by a method similar to that described in Example 5, but in this Example 0.03 part per hour of trimethyl phosphate, $(CH_3O)_3PO$ (corresponding to 30 ppm of P, based on the weight of ethylene glycol fed in), is added to the gas mixture flowing over the catalyst.

357 parts per hour of a 42 percent strength by weight glyoxal solution, ie. 150 parts of glyoxal per hour, are obtained, corresponding to a yield of 72.9% of theory, based on the glycol used.

The glyoxal solution contains 1.1 percent by weight of ethylene glycol, 0.8 percent by weight of formaldehyde and 3.5 percent by weight of glycolaldehyde and has an acid number of 3. The conversion is 98.2 percent, the space/time yield is 16.0 g of glyoxal per cm³ of catalyst volume per hour, and the color number of the solution after three days of operation is 9.

The essential results of the Examples according to the invention and of the Comparative Examples are summarized in the Table. It becomes clear that the glyoxal yield is substantially higher and the content of troublesome impurities in the glyoxal solution which are difficult to separate off is substantially lower when the copper/silver layered catalyst (1) according to the invention is used than when a pure silver or copper catalyst (2 and 3 respectively) or a copper/silver mixture (4) is used. The addition, according to the invention, of 3 ppm of phosphorus (5) has the effect of additionally increasing the yield while slightly improving the product quality. However, if the amount of phosphorus is increased beyond the optimum value (6, with 30 ppm of phosphorus), the yield drops and the product quality is poorer.

| Example | Conversion of glycol (%) | Yield of glyoxal (%) | Content of by-products based on 40% strength glyoxal solution | | | Acid number (1) | Color number (2) |
| --- | --- | --- | --- | --- | --- | --- | --- |
| | | | glycol (% by weight) | glycolaldehyde (% by weight) | formaldehyde (% by weight) | | |
| 1 (according to the invention) | 99.9 | 70.6 | 0.05 | 0.9 | 1.2 | 4 | 12 |
| 2 (comparative) | 97.9 | 60.3 | 1.5 | 7.6 | 1.1 | 5 | 19 |
| 3 (comparative) | 94.4 | 54.9 | 4.4 | 1.4 | 1.1 | 6 | 24 |
| 4 (comparative) | 96.9 | 57.8 | 2.3 | 5.1 | 1.3 | 5 | 18 |
| 5 (according to the invention) | 99.9 | 77.3 | 0.04 | 0.9 | 0.9 | 4 | 10 |
| 6 | 98.2 | 72.9 | 1.0 | 3.3 | 0.8 | 3 | 9 |

| | | | Content of by-products based on 40% strength glyoxal solution | | | | |
|---|---|---|---|---|---|---|---|
| Example | Conversion of glycol (%) | Yield of glyoxal (%) | glycol (% by weight) | glycolaldehyde (% by weight) | formaldehyde (% by weight) | Acid number (1) | Color number (2) |
| (comparative) | | | | | | | |

(1) Amount of potassium hydroxide, in mg, required for neutralizing 1 g of glyoxal solution
(2) Determination by means of the platinum/cobalt scale according to ASTM D 1209-69

We claim:

1. A process for the continuous preparation of glyoxal by oxidation of ethylene glycol, which comprises: passing ethylene glycol, oxygen and an inert gas continuously at from 450° to 800° C. over a catalyst consisting essentially of copper and silver, said catalyst consisting essentially of one or more layers of copper crystals and one or more layers of silver crystals, the copper and silver crystals having a particle size of from 0.1 to 2.5 mm.

2. The process of claim 1, wherein the oxidation is carried out in the presence of a phosphorus compound which is volatile under the reaction conditions, the amount of phosphorus (calculated as P) being from 0.5 to 20 ppm, based on the amount by weight of ethylene glycol.

3. The process of claim 1, wherein the amount of silver crystals is from 55 to 90% by weight, based on the total weight of the catalyst.

4. The process of claim 1, wherein the catalyst consists of from one to four layers of copper crystals and from one to four layers of silver crystals.

5. The process of claim 1, wherein the catalyst consists of two or three layers of copper crystals and two or three layers of silver crystals.

6. The process of claim 2, wherein the phosphorus compound is selected from the group consisting of trimethyl phosphate, triethyl phosphate, tri-isopropyl phosphate, tri-n-propyl phosphate, trimethyl phosphite, triethyl phosphite, triethylphosphine oxide, diethyl methylphosphonate, dimethyl methylphosphonate and diethyl ethylphosphonate.

* * * * *